United States Patent [19]

Murphy

[11] 4,320,231

[45] Mar. 16, 1982

[54] AQUEOUS SOLUTIONS OF DIALDEHYDES AND KETONES

[75] Inventor: Gerald J. Murphy, Wappinger Falls, N.Y.

[73] Assignee: Union Carbide Corporation, New York, N.Y.

[21] Appl. No.: 208,810

[22] Filed: Nov. 20, 1980

[51] Int. Cl.³ .................. C07C 45/78; C07C 47/12
[52] U.S. Cl. ............................. 568/494; 568/304; 568/382; 568/421
[58] Field of Search ............... 568/494, 421, 303, 420, 568/345, 390, 496, 497, 304, 382, 448

[56] References Cited

U.S. PATENT DOCUMENTS

| | | | |
|---|---|---|---|
| 2,333,182 | 11/1943 | Jones | 568/494 |
| 2,801,216 | 7/1957 | Yoder et al. | 568/421 |
| 2,809,186 | 10/1957 | Smith et al. | 568/494 |
| 3,637,858 | 1/1972 | Dinwoodie et al. | 568/421 |
| 4,146,581 | 3/1979 | Nissen | 568/345 |
| 4,244,876 | 1/1981 | Warner et al. | 568/421 |

*Primary Examiner*—Werren B. Lone
*Attorney, Agent, or Firm*—Donald M. Papuga

[57] ABSTRACT

Described herein is an aqueous solution comprising a dialdehyde of from 2 to 6 carbon atoms and an aliphatic ketone. This solution may be stored under conditions under which the aqueous dialdehyde solution would normally freeze.

6 Claims, No Drawings

AQUEOUS SOLUTIONS OF DIALDEHYDES AND KETONES

The invention is directed to an aqueous solution comprising a dialdehyde of from 2 to 6 carbon atoms and an aliphatic ketone. This solution may be stored under conditions under which the aqueous dialdehyde solution would normally freeze.

Aqueous solutions of glutaraldehyde are well known commercially available materials useful for killing or inhibiting the growth of microorganisms. These aqueous solutions of glutaraldehyde have been used to control the growth of bacteria in a number of different environments. For example, glutaraldehyde solutions have been used to disinfect medical and surgical supplies and household objects. Further, as described in U.S. Pat. No. 2,801,216 glutaraldehyde solutions have been used to control bacteria in water flooding operations for the secondary recovery of oil and used to prevent corrosion and plugging of iron equipment due to the action of bacteria in storage vessels and associated plumbing and equipment. Thus, it can be seen that there are occasions when glutaraldehyde solutions are stored out of doors and may be subjected to freezing conditions. The freezing point of a 25 percent aqueous solution of glutaraldehyde is about 22° F. Therefore, it would be desirable under these conditions to further depress the freezing point of the aqueous solution of glutaraldehyde. However, any additive to the aqueous glutaraldehyde solution which could depress the freezing point of the solution must not decrease the biological activity of the solution and must be one which maintains the freezing point at the desired temperature. That is, the additive should be one which is able to maintain the desired temperature over extended periods of time. For example, ethylene glycol is known to react with glutaraldehyde so that even though addition of ethylene glycol to an aqueous soluton of glutaraldehyde initially depresses the freezing point, upon storage, the freezing point rises as the glycol reacts with glutaraldehyde to form a blend containing acetal linkages.

DESCRIPTION OF THE INVENTION

It has now been found that the addition of a water soluble aliphatic ketone to an aqueous solution of one or more dialdehydes containing 2 to 6 carbon atoms depresses the freezing point of the aqueous solution of the dialdehydes without effecting biological activity of the dialdehyde solution. Since the ketone and dialdehyde do not react, their aqueous solutions maintain their depressed freezing point over an extended period of time.

The dialdehydes which may be employed in this invention are one or more saturated dialdehydes containing from 2 to 6 carbon atoms. These dialdehydes include oxaldehyde (glyoxal), adipaldehyde, and preferably, glutaraldehyde.

The aliphatic ketones which may be used herein include one or more aliphatic ketone containing from 3 to 6 carbon atoms, such as acetone and methyl ethyl ketone, and mixtures thereof. The preferred ketone is acetone.

The aqueous solution contains from about 0.1 to about 50 percent by weight of the dialdehyde; from about 5 to about 40 percent by weight of the ketone with the remainder of the solution being water such that the total solution is 100 percent by weight. A preferred solution contains 25 percent by weight of dialdehyde, 30 percent by weight of acetone and 45 percent by weight of water.

The solutions may contain other additives such as colorants, surfactants, chelating agents, pH buffers and the like.

EXAMPLES

The following examples serve to give specific illustrations of the practice of this invention but they are not intended in any way to limit the scope of this invention.

CONTROL A

The freezing point of a mixture of 25 percent by weight of glutaraldehyde and 75 percent by weight of water is 22° F. (as determined by the procedure as set forth in ASTM D-1177-65).

EXAMPLES 1 TO 5

In all of these Examples, the value of the freezing point of the mixture is an average of two readings.

EXAMPLE 1

The following ingredients were mixed:
25 percent by weight of glutaraldehyde,
15 percent by weight of acetone, and
60 percent by weight of water.
The freezing point of the mixture was 4.4.

EXAMPLE 2

The following ingredients were mixed:
25 percent by weight of glutaraldehyde,
20 percent by weight of acetone, and
55 percent by weight of water.
The freezing point of the mixture was −2.5° F.

EXAMPLE 3

The following ingredients were mixed:
25 percent by weight of glutaraldehyde,
22 percent by weight of acetone, and
50 percent by weight of water.
The freezing point of the mixture was −10.6° F.

EXAMPLE 4

The following ingredients were mixed:
25 percent by weight of glutaraldehyde,
30 percent by weight of acetone, and
45 percent by weight of water.
The freezing point of the mixture was −17.5° F.

EXAMPLE 5

The following ingredients were mixed:
25 percent by weight of glutaraldehyde,
35 percent by weight of acetone, and
40 percent by weight of water.
The freezing point of the mixture was −20.1° F.
Examples 1 to 5 are summarized in the Table.

TABLE

| Example | Percent Acetone by weight | Freezing Point (°F.) |
|---|---|---|
| Control A | 0 | 22 |
| 1 | 15 | 4.4 |
| 2 | 20 | −2.5 |
| 3 | 25 | −10.6 |
| 4 | 30 | −17.5 |
| 5 | 35 | −20.2 |

The determination of the freezing point depression of varying concentrations of dialdehyde and water by the addition of ketone can be easily determined by following the above examples.

EXAMPLE 6

A mixture of the same composition as that in Example 3 was stored at about 25° C. for 55 days and the freezing point was then measured. It was −9.8° F.

CONTROL B

The following ingredients were mixed:
25 percent by weight of glutaraldehyde,
25 percent by weight of methanol, and
50 percent by weight of water.

The freezing point of the mixture was −20.5° F. After storage for 55 days at about 25° C., the freezing point of the mixture was measured and found to be −9.5° F.

CONTROL C

The following ingredients were mixed:
25 percent by weight of glutaraldehyde,
25 percent by weight of ethylene glycol, and
50 percent by weight of water.

The freezing point of the mixture was −14.0° F. After storage for 55 days at about 25° C., the freezing point of the mixture was measured and found to be −7.5° F.

As shown by Example 6, the compositions of this invention essentially maintains its freezing point after 55 days of storage whereas when methanol and ethylene glycol are used as freezing point depressants (Controls B and C) the freezing point has substantially increased after storage.

What is claimed is:

1. An aqueous solution comprising a saturated dialdehyde containing from 2 to 6 carbon atoms and from about 5 to about 40 percent by weight of an aliphatic ketone containing from 3 to 6 carbon atoms.

2. A solution as defined in claim 1 wherein the dialdehyde is glutaraldehyde.

3. A solution as defined in claim 1 wherein the ketone is acetone.

4. A solution as defined in claim 1 wherein the dialdehyde is glutaraldehyde and the ketone is acetone.

5. An aqueous solution comprising 25 percent by weight of glutaraldehyde, 30 percent by weight of acetone and 45 percent by weight of water.

6. An aqueous solution comprising a saturated dialdehyde containing from 2 to 6 carbon atoms and an aliphatic ketone containing from 3 to 6 carbon atoms, wherein the ketone is present in an amount which depresses the freezing point of the aqueous solution.

* * * * *